US007488286B2

(12) United States Patent
James et al.

(10) Patent No.: US 7,488,286 B2
(45) Date of Patent: Feb. 10, 2009

(54) ENDOSCOPE CAP CONNECTOR AND METHOD OF USING SAME

(75) Inventors: Michael James, Oceanside, CA (US); Michael Munoz, Chula Vista, CA (US)

(73) Assignee: San Diego Endoscopic Products, LLC

( * ) Notice: Subject to any disclaimer, the term of this patent is extended or adjusted under 35 U.S.C. 154(b) by 577 days.

(21) Appl. No.: 10/854,124

(22) Filed: May 26, 2004

(65) Prior Publication Data
US 2004/0254421 A1    Dec. 16, 2004

Related U.S. Application Data

(60) Provisional application No. 60/473,548, filed on May 28, 2003.

(51) Int. Cl.
*A61B 1/00* (2006.01)
(52) U.S. Cl. ..................... 600/154; 600/133
(58) Field of Classification Search ............. 24/30.5 R, 24/30.5 P, 30.5 W, 3.13; 215/306, 289, 227, 215/278, 258; 600/101–183
See application file for complete search history.

(56) References Cited

U.S. PATENT DOCUMENTS

| | | | | |
|---|---|---|---|---|
| 4,054,221 A | * | 10/1977 | Glover | 215/235 |
| 5,513,768 A | * | 5/1996 | Smith | 220/259.2 |
| 5,784,760 A | * | 7/1998 | Leitzke et al. | 24/3.13 |
| 5,993,379 A | * | 11/1999 | Ouchi et al. | 600/119 |
| 6,011,617 A | * | 1/2000 | Naudet | 356/237.1 |
| 6,117,070 A | * | 9/2000 | Akiba | 600/154 |
| 6,227,399 B1 | * | 5/2001 | Angus et al. | 220/375 |
| 6,276,029 B1 | * | 8/2001 | Buettell | 24/30.5 P |
| 6,443,888 B1 | * | 9/2002 | Ogura et al. | 600/132 |
| 6,588,622 B1 | * | 7/2003 | Leishman et al. | 220/719 |
| 6,606,768 B2 | * | 8/2003 | Henry et al. | 24/306 |
| 2002/0013510 A1 | * | 1/2002 | Moriyama | 600/118 |
| 2003/0088155 A1 | * | 5/2003 | Ishibiki | 600/127 |

OTHER PUBLICATIONS

Olympus Medical Systems Corp., Instructions, Chain For Water-Resistant Cap (MAJ-1119), Jun. 1, 2005 (?), 2 pages, Japan.

* cited by examiner

Primary Examiner—John P. Leubecker
Assistant Examiner—Victoria W Chen

(57) ABSTRACT

An appliance is provided for connecting the water-tight cap of an endoscope using the distal end of the appliance to connect the water-tight cap over a venting pin connector to the proximal body of the endoscope or bronchoscope over the "S" connector by the proximal end of the appliance. In one version of the invention, one end of the appliance is connected to the "S" connector of the proximal body of the endoscope, as described in detail herein. In another version of the invention, one end of the appliance is wrapped around the proximal body of the endoscope, as described in detail herein. The invention also includes methods of operating the appliance.

26 Claims, 2 Drawing Sheets

ENDOSCOPE CAP CONNECTOR AND METHOD OF USING SAME

CROSS REFERENCE TO OTHER APPLICATIONS

This application claims the benefit of U.S. provisional application No. 60/473,548, filed on May 28, 2003. The full disclosure of this provisional application is incorporated herein by reference.

BACKGROUND

The present invention relates generally to means of attaching components comprising various medical devices. More specifically, the present invention relates to an appliance used to removably connect the water-tight cap of an endoscope to the proximal body of the endoscope.

Modern endoscopes and bronchoscopes are generally comprised of a proximal body portion and a tubing portion, which is connected to the proximal body portion. The tubing portion comes into contact with the patient while the endoscope or bronchoscope is being used for patient treatment, but the proximal body portion does not generally come into contact with the patient during such treatment. Various electrical and optical leads are connected to the proximal body portion. Among them is a cable related to the video/optical imaging of the endoscope. At the point of connection of this cable with the proximal body portion of the endoscope or bronchoscope, there a connector that typically has a series of electrical contact pins, among other items. When the endoscope or bronchoscope undergoes its periodic cleaning and leak testing, which involves submerging the proximal body portion in various fluids, the video/optical cable is removed from the connector on the proximal body portion of the endoscope and a water-tight cap is used to cover the connector. The water-tight cap is then removed from the proximal body portion prior to operation of the endoscope or bronchoscope for patient treatment.

When the water-tight cap is removed from the endoscope or bronchoscope, the cap is often set aside until it is needed again. When this occurs, the cap may be misplaced or lost. In addition, the water-tight cap is sometimes dropped after it has been removed from the body of the endoscope or bronchoscope. The resulting fall can produce cracks or other damage that render the cap unusable. In either case, it becomes necessary to replace the water-tight cap. Because the cost of replacing a water-tight cap is relatively high (in excess of U.S. $250 as of the date of filing of this patent application), there is a need for a means to prevent this loss of and damage to the water-tight cap while it is removed. Any such means must, however, meet other requirements to be appropriate for this purpose. For example, the means must not interfere with the operation of the endoscope or bronchoscope. In addition, the means must operate in a manner that does not cause undue accumulation of bacteria and other harmful foreign material. Further, the means must be resilient enough to withstand the rigorous demands that accompany modern use of endoscopes and bronchoscopes.

SUMMARY

The present invention is directed to an appliance and methods of using the appliance that meet the needs discussed above in the Background section. As described in greater detail below, the present invention, when used for its intended purpose, has many advantages over other appliances known in the art, as well as novel features that result in a new appliance and methods that are not anticipated, rendered obvious, suggested, or even implied by any prior art devices or methods, either alone or in any combination thereof.

Generally, the present invention is comprised of an appliance, and methods for its operation, used to connect the water-tight cap portion of an endoscope or bronchoscope with the proximal body portion of the endoscope or bronchoscope, respectively. For simplicity, and except where the differences are pertinent, only an "endoscope" is referred to herein. It is to be understood, however, that such references apply generally to both endoscopes and bronchoscopes except where otherwise noted. The water-tight cap portion of the endoscope is comprised of a cap body that is adapted to be removably attached to, and to cover the appropriate connector opening on, the proximal body of the endoscope. In certain models of endoscopes, the cap body also has a venting connector located on one of its surfaces. The venting connector is used to connect the endoscope to a source of compressed air or other gas for purposes of leak testing the endoscope. The venting connector is generally comprised of a somewhat cylindrical or conical metal connector having a pin protruding approximately perpendicularly from one of its surfaces. A leak testing cap is adapted to fit over and be removably attached to the venting connector. In addition, in certain models of endoscopes, the proximal body of the endoscope also has an "S" connector. The "S" connector, which is typically cylindrical or conical in shape, is generally protruding approximately perpendicularly from one of the surfaces of the proximal body of the endoscope. The distal portion of the "S" connector typically has a diameter greater than the diameter of the "S" connector adjacent to the surface of the proximal body of the endoscope. The "S" connector is generally used for purposes of further diagnostic tests. It is to be noted, however, that this description of the endoscope and its component parts is for reference purposes only; neither the endoscope nor any of its component parts, including the water-tight cap portion and the proximal body portion, are a part of the present invention.

The appliance is comprised of a connecting member portion having a proximal end portion at one end of the connecting member portion and a distal end portion at the other end of the connecting member portion. The proximal end portion is adapted to be removably connected to the proximal body portion of the endoscope. The distal end portion is adapted to be removably connected to the water-tight cap portion of the endoscope. In one version of the invention, the distal end portion of the appliance is comprised of a disc with a perimeter that is preferably approximately circular in shape. The disc has an aperture therein of a shape and size adapted to fit over the metal connector and pin of the venting connector, allowing the distal end portion to slide down the metal connector to the surface of the body of the water-tight cap. When the distal end portion is removably attached to the water-tight cap, the distal end portion is held adjacent to the surface of the water-tight cap by the leak testing cap.

In some embodiments of this version of the invention, the aperture within the distal end portion is approximately "tear drop" in shape, so that the elongated portion of the aperture is adapted to fit tightly over the pin portion of the venting connector. Other shapes, however, may be used, as described in more detail below. Preferably, the dimension of the aperture longitudinally along the longest axis of the aperture is approximately 6/16 inches, and the dimension of the aperture axially along the shortest axis of the aperture is approximately 4/16 inches. In other embodiments of this version of the invention, the disc comprising the distal end portion preferably has a thickness in the range of approximately 0.05 inches to approximately 0.15 inches. In yet other embodiments of this version of the invention, the diameter of the outer periphery of the disc comprising the distal end portion is approximately $10/16$ inches.

In this version of the invention, the proximal end portion of the connecting member is comprised of a disc that is approximately circular in shape. The disc has an aperture therein that is preferably generally circular in shape and is of a size adapted to fit over the "S" connector, allowing the distal end portion to slide down the surface of the "S" connector to the surface of the proximal body portion of the endoscope. In other embodiments of this version of the invention, the aperture may be of other shapes, as described in more detail below. When the proximal end portion is removably attached to the proximal body portion of the endoscope, the proximal end portion is held adjacent to the surface of the proximal body portion of the endoscope by the distal portion of the "S" connector, which has a greater diameter than the diameter of the aperture. Preferably, the dimension of the aperture within the disc comprising the proximal end portion is in the range of approximately $3/16$ inches to approximately $4/16$ inches. In other embodiments of this version of the invention, the disc comprising the proximal end portion preferably has a thickness in the range of approximately 0.05 inches to approximately 0.15 inches. In yet other embodiments of this version of the invention, the diameter of the outer periphery of the disc comprising the proximal end portion is approximately $10/16$ inches.

In some embodiments of this version of the invention, the connecting member portion between the proximal end portion and the distal end portion is preferably generally shaped as a rectangle, but may be of other shapes, as described in more detail below. In some embodiments of this version of the invention, the length of the connecting member portion between the points of connection of such connecting member portion with the proximal end portion and the distal end portion is in the range of approximately 2½ inches to approximately five inches when measured along the longitudinal axis of the connecting member and the width of the connecting member portion is in the range of approximately $5/16$ inches to approximately $7/16$ inches when measured perpendicular to the longitudinal axis. In other embodiments of this version of the invention, the connecting member portion further comprises portions that protrude outwardly from each of the two longest sides of the rectangle, wherein such protruding portions may be of various shapes, but are preferably generally elliptical in shape and are centered about the midpoint of such sides. In some embodiments of this version of the invention, the appliance is comprised of a flexible polymer material. Preferably, the appliance is comprised of latex-free, neoprene rubber. In yet other embodiments of this version of the invention, the appliance further comprises an antibacterial coating on all of the surfaces thereof.

In another version of the invention, the proximal end portion is comprised of a disc that is approximately circular in shape and an elongated portion of the connecting member portion. The elongated portion is an extension of the connecting member portion, being located between the connecting member and the disc comprising the proximal end portion. The periphery of the disc has a diameter of approximately $10/16$ inches. The disc also has an aperture therein that is preferably approximately circular in shape with a diameter of approximately $4/16$ inches, but may be of other shapes as described in more detail below. In this version of the invention, the elongated portion and the disc comprising the proximal end portion are wrapped around the proximal body portion of the endoscope and the distal end portion is pulled through the aperture in the proximal end portion until the proximal end portion is held tightly against the surface of the proximal body of the endoscope. Preferably, the connecting member portion and the elongated portion are generally in the shape of a rectangle. In addition, the sum of the lengths of the connecting member portion and the elongated portion as measured between the point of connection of the connecting member portion with the distal end portion and the point of connection of the elongated portion with the proximal end portion is preferably in the range of approximately seven inches to approximately nine inches, and the width of the connecting member portion and the elongated portion are approximately the same and in the range of approximately $5/16$ inches to approximately $7/16$ inches when measured perpendicular to their longitudinal axis. The other aspects of this version of the invention are substantially the same as those discussed above for the first version of the invention. In other embodiments of this version of the invention, the connecting member portion further comprises portions that protrude outwardly from each of the two longest sides of the rectangle, wherein such protruding portions are preferably generally elliptical in shape and are centered about the midpoint of such sides.

The present invention also includes methods of using the appliance. A method for connecting the first version of the invention discussed above to an endoscope is comprised of the following steps: (1) removing the leak testing cap from the venting connector on the water-tight cap; (2) placing the aperture of the distal end portion over the venting connector, stretching the aperture of the distal end portion of the appliance over the venting connector, sliding the distal end portion along the venting connector until the distal end portion is adjacent to the surface of the body of the water-tight cap, and removably attaching the leak testing cap to the venting connector; and (3) stretching the aperture in the proximal end of the appliance over the "S" connector on the proximal body portion of the endoscope, and sliding the proximal end along the surface of the "S" connector until the proximal end portion is adjacent to the surface of the proximal body of the endoscope. Steps (1) through (3), above, can be performed in any order. The appliance can be removed by reversing steps (1) through (3), above, in any order.

A method for connecting the second version of the invention discussed above to an endoscope is comprised of the following steps: (1) wrapping the proximal end portion around the proximal body portion of the endoscope, placing the distal end portion through the aperture in the proximal end portion, and pulling the distal end portion through the aperture in the proximal end portion until the proximal end portion is held tightly against the surface of the proximal body of the endoscope; and (2) removing the leak testing cap from the venting connector on the water-tight cap, placing the aperture of the distal end portion over the venting connector, stretching the aperture of the distal end portion of the appliance over the venting connector, sliding the distal end portion along the venting connector until the distal end portion is adjacent to the surface of the body of the water-tight cap, and removably attaching the leak testing cap to the venting connector. Steps (1) and (2) of this second method are to be performed in the order presented. The appliance may be removed by reversing steps (1) and (2) of this second method in the order presented.

As described in more detail below, the appliance successfully meets all of the requirements described in the Background section above. For example, the operation of the appliance does not interfere with the operation of the endoscope. In addition, the appliance operates in a manner that does not cause undue accumulation of bacteria and other harmful foreign material. Finally, the appliance is resilient enough to withstand the rigorous demands that accompany modern use of endoscopes.

There has thus been outlined, rather broadly, the more primary features of the present invention. There are additional features that are also included in the various embodiments of the invention that are described hereinafter and that form the subject matter of the claims appended hereto. In this respect, it is to be understood that the invention is not limited in its application to the details of construction and to the arrangements of the components set forth in the following description or illustrated in the following drawings. This invention may be embodied in the form illustrated in the accompanying drawings, but the drawings are illustrative only and changes may be made in the specific construction illustrated and described within the scope of the appended claims. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

The foregoing summary, as well as the following description, will be better understood when read in conjunction with the appended drawings, in which.

DESCRIPTION

Reference will now be made in detail to the preferred aspects, versions and embodiments of the present invention, examples of which are illustrated in the accompanying drawings. While the invention will be described in conjunction with the preferred aspects, versions and embodiments, it is to be noted that the versions and embodiments are not intended to limit the invention to those aspects, versions and embodiments. On the contrary, the invention is intended to cover alternatives, modifications and equivalents, which may be included within the spirit and scope of the invention as defined by the appended claims.

Figure 1A:
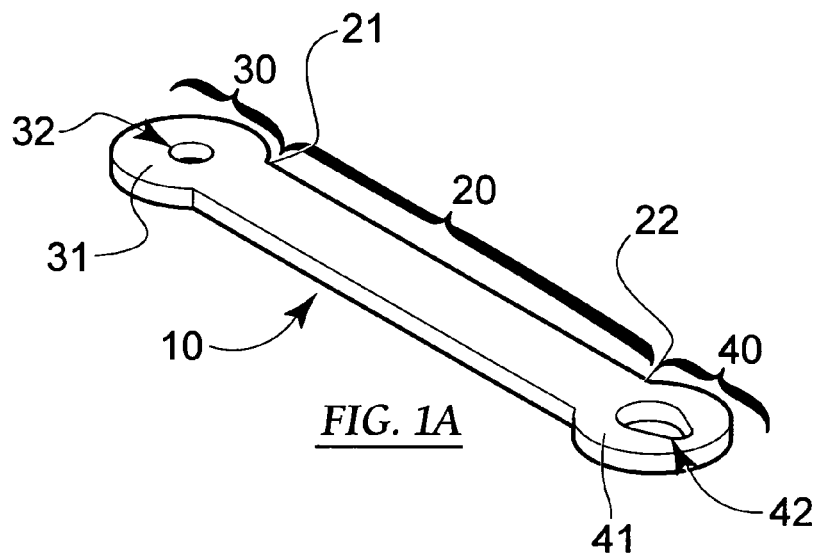
FIG. 1A is a perspective view of one version of the invention from above the surface thereof.

One version of the present invention is illustrated in FIG. 1A. The appliance 10 of this version is comprised of a connecting member portion 20 having a proximal end portion 30 at one end of the connecting member portion 20 and a distal end portion 40 at the other end of the connecting member portion 20. The connecting member portion 20 is sometimes referred to as the "connecting member" herein, the proximal end portion 30 is sometimes referred to as the "proximal end" herein, and the distal end portion 40 is sometimes referred to as the "distal end" herein. The proximal end 30 and the distal end 40 are adapted to be connected to various portions of an endoscope or bronchoscope, as described in more detail below.

Figure 2:
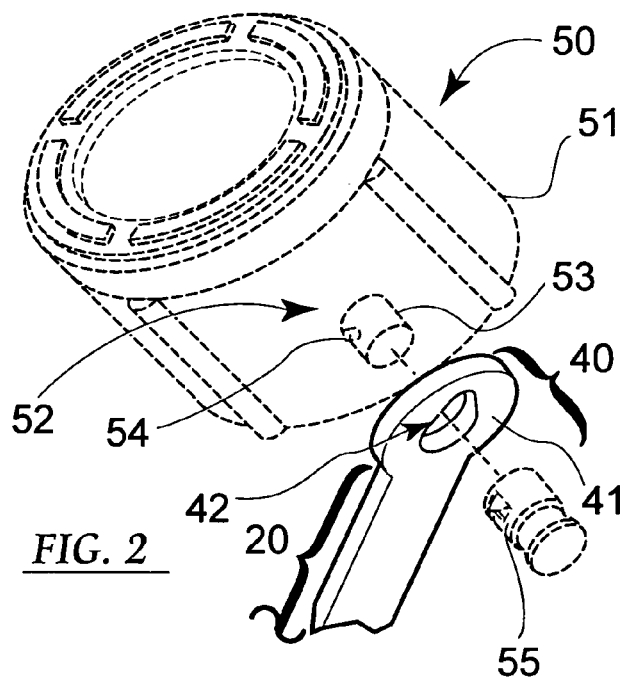
FIG. 2 is an exploded component view illustrating the removable connection of the appliance in the version of the invention illustrated in FIG. 1A to the water-tight cap of an endoscope, the water-tight cap being illustrated for reference only.
Figure 3:
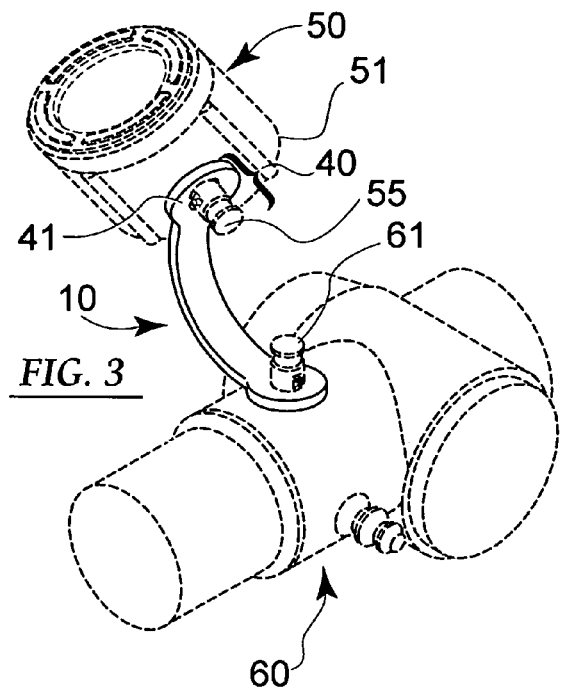
FIG. 3 is a perspective view of the embodiment of the invention illustrated in FIG. 1A, with the appliance removably connected to the water-tight cap and the proximal body of an endoscope, the water-tight cap and the proximal body being illustrated for reference only.

It is to be noted that while certain embodiments of the invention may be used with other brands of endoscopes, the invention is preferably used with flexible endoscopes and bronchoscopes sold under the trademark OLYMPUS, to include sigmoidoscopes, colonoscopes, esophagealgastroduodenal scopes, and endoscopic retrograde cholangiopancreatography procedure scopes and the like. For simplicity, and except where the differences are pertinent, only an "endoscope" is referred to herein. It is to be understood, however, that such references apply generally to both endoscopes and bronchoscopes except where otherwise noted. As discussed above in the Background and Summary sections, and as illustrated in FIG. 2, the water-tight cap portion 50 of the endoscope is comprised of a cap body 51 that is adapted to be removably attached to, and to cover the appropriate connector opening on, the proximal body portion of the endoscope. The water-tight cap portion 50 is sometimes referred to as the "water-tight cap" herein. In certain models of endoscopes, the cap body 51 also has a venting connector 52 located on one of its surfaces. The venting connector 52 is generally comprised of a somewhat cylindrical or conical metal connector 53 having a pin 54 protruding approximately perpendicularly from one of its surfaces. A leak testing cap 55 is adapted to fit over and be removably attached to the venting connector 52. Also, as discussed above in the Background and Summary sections, and as illustrated in FIG. 3, in certain models of endoscopes (including the OLYMPUS endoscopes), the proximal body portion 60 of the endoscope also has an "S" connector 61. The "S" connector 61, which is typically cylindrical or conical in shape, is generally protruding approximately perpendicularly from one of the surfaces of the proximal body portion 60 of the endoscope. The distal portion of the "S" connector 61 typically has a diameter greater than the diameter of the "S" connector 61 adjacent to the surface of the proximal body portion 60 of the endoscope. The proximal body portion 60 of the endoscope is sometimes referred to herein as the "proximal body" of the endoscope. It is to be noted, however, that the above description of the endoscope and its component parts is for reference purposes only; neither the endoscope nor any of its component parts, including the water-tight cap 50 and the proximal body 60, are a part of the present invention.

In the version of the invention illustrated in FIG. 1A, the distal end 40 of the appliance 10 is comprised of a disc 41 with a perimeter that is approximately circular in shape. The disc 41 has an aperture 42 therein. As illustrated in FIG. 2, the aperture 42 is of a shape and size adapted to fit over the metal connector 53 and pin 54 of the venting connector 52 of the water-tight cap 50, allowing the distal end 40 to slide down the metal connector 53 to the surface of the body 51 of the water-tight cap 50. The leak testing cap 55 is then removably attached to the venting connector 52 over the distal end 40. When the distal end 40 is removably attached to the water-tight cap 50, as illustrated in FIG. 3, the distal end 40 is held adjacent to the surface of the body 51 of the water-tight cap 50 by the leak testing cap 55. In the embodiment of the version of the invention illustrated in FIG. 1A and FIG. 2, the aperture 42 in the distal end 40 is approximately "tear drop" in shape, so that the aperture 42 is adapted to fit tightly over the pin 54 and metal connector 53 of the venting connector 52. Preferably, the dimension of the aperture 42 longitudinally along the longest axis of the aperture 42 is approximately 6/16 inches, and the dimension of the aperture 42 axially along the shortest axis of the aperture 42 is approximately 4/16 inches. These dimensions allow the aperture 42 in the distal end 40 to pass over the pin 54 and the metal connector 53, but cause the aperture 42 to be smaller than the diameter of the leak testing cap 55. It is to be noted, however, that although the "tear drop" shape is the preferred shape, other shapes may also be used that have the same general dimensions along their axes of maximum and minimum dimension. As a result, and as illustrated in FIG. 3, when the leak testing cap 55 is removably attached to the venting connector 52, the leak testing cap 55 holds the distal end 40 against the surface of the body 51 of the water-tight cap 50.

In addition, in the embodiment of the version of the invention illustrated in FIG. 1A, FIG. 2, and FIG. 3, the disc 41 comprising the distal end 40 preferably has a thickness in the range of approximately 0.05 inches to approximately 0.15 inches. This thickness allows the distal end 40 to rest between the surface of the body 51 of the water-tight cap 50 and the lower surface of the leak testing cap 55. Thicknesses greater than approximately 0.15 inches would generally prevent the leak testing cap 55 from being removably connected to the venting connector 52. Thicknesses less than 0.05 inches may cause the distal end 40 to have insufficient structural strength to hold the water-tight cap 50 during normal usage of the appliance 10, causing the distal end 40 to break, thereby releasing the water-tight cap 50. Further, in the embodiment of the version of the invention illustrated in FIG. 1A, FIG. 2, and FIG. 3, the preferred diameter of the outer periphery of the disc 41 comprising the distal end 40 is approximately 10/16 inches. Diameters less than approximately 10/16 inches may cause the distal end 40 to have insufficient structural strength to hold the water-tight cap 50 during normal usage of the appliance 10, causing the distal end 40 to break, thereby releasing the water-tight cap 50. Diameters greater than approximately 10/16 inches tend to create too much friction when the leak testing cap 55 is removably attached to and removed from the venting connector 52, and also tend to cause the distal end 40 to unnecessarily interfere with operation of the endoscope. In addition, it should be noted that all of these dimensions allow for adequate flushing of the area surrounding the venting connector 52, leak testing cap 55, and body 51 of the water-tight cap 50, as well as the distal end 40, during cleaning of the water-tight cap 50 while the appliance 10 is attached to the water-tight cap 50. This flushing prevents the buildup of foreign material that can cause bacterial and other detrimental infestations in these areas.

In the version of the invention illustrated in FIG. 1A and FIG. 3, the proximal end 30 of the appliance 10 is comprised of a disc 31 with a perimeter that is preferably approximately circular in shape. In the illustrated embodiment, the disc 31 has an aperture 32 therein that is approximately circular in shape. As illustrated in FIG. 2 and FIG. 3, the aperture 32 is of a size and shape adapted to fit over the "S" connector 61 of the proximal body 60 of the endoscope, allowing the proximal end 30 to slide down the "S" connector 61 to the surface of the proximal body 60 of the endoscope. When the proximal end 30 is removably attached to the proximal body 60 of the endoscope, the proximal end 30 is held adjacent to the surface of the proximal body 60 of the endoscope by the distal portion of the "S" connector 61 having a greater diameter than the diameter of the aperture 32. In this version of the invention, the diameter of the aperture 32 within the disc 31 comprising the proximal end 30 is preferably in the range of approximately 3/16 inches to approximately 4/16 inches, and most preferably 3/16 inches. This dimension allows the aperture 32 in the proximal end 30 to pass over the "S" connector 61, but causes the aperture 32 to be smaller than the diameter of the distal end of the "S" connector 61. As a result, and as illustrated in FIG. 3, when the aperture 32 of the proximal end 30 is placed over the "S" connector 61 and pushed down against the surface of the proximal body 60 of the endoscope, the proximal end 30 is held against the surface of the proximal body 60 of the endoscope by the distal portion of the "S" connector 61. It is to be noted, however, that although the aperture 32 is preferably approximately circular in shape, other shapes may also be used as long as the dimensions associated with such shapes allows for the proximal end 30 to be held against the proximal body 60 of the endoscope by the distal portion of the "S" connector 61 when the appliance 10 is removably connected to the proximal body 60 of the endoscope. For example, the aperture 32 may be in the shape of a four-leaf clover or a star having five points where the minimum dimension of such aperture 32, as generally measured across the closest opposing sides of such aperture, is in the range of approximately 3/16 inches to approximately 4/16 inches.

In addition, in the embodiment of the version of the invention illustrated in FIG. 1A and FIG. 3, the disc 31 comprising the proximal end 30 preferably has the same thickness as the distal end 40 (a thickness in the range of approximately 0.05 inches to approximately 0.15 inches), to simplify manufacturing of the appliance 10. This thickness allows the proximal end 30 to rest between the surface of the proximal body 60 of the endoscope and the distal portion of the "S" connector 61, which generally has a diameter greater than that of the aperture 32. In addition, this thickness provides sufficient structural strength to hold the appliance 10 to the proximal body 60 of the endoscope during normal usage of the appliance 10. Further, in the embodiment of the version of the invention illustrated in FIG. 1A and FIG. 3, the preferred diameter of the outer periphery of the disc 31 comprising the proximal end 30 is approximately 10/16 inches. Diameters less than approximately 10/16 inches may cause the proximal end 30 to have insufficient structural strength to hold the proximal body 60 of the endoscope during normal usage of the appliance 10, causing the proximal end 30 to break, thereby releasing the water-tight cap 50. Diameters greater than approximately 10/16 inches tend to cause the proximal end 30 to unnecessarily interfere with operation of the endoscope. In addition, as in the case of the distal end 40, all of the dimensions for the proximal end 30 allow for adequate flushing of the area surrounding the "S" connector 61 and proximal body 60 of the endoscope, as well as the proximal end 30, during cleaning of the proximal body 60 of the endoscope while the appliance 10 is attached to the proximal body 60 of the endoscope. This flushing prevents the buildup of foreign material that can cause bacterial and other detrimental infestations in these areas.

In the version of the invention illustrated in FIG. 1A, FIG. 2, and FIG. 3, the connecting member 20 between the proximal end 30 and the distal end 40 is generally in the shape of a rectangle. Although the connecting member 20 may be of other shapes, such as a cylinder, the rectangle is the preferred shape. In this embodiment and version of the invention, the length of the connecting member 20, as measured between the point of attachment 21 of the connecting member 20 with the proximal end 30 and the point of attachment 22 of the connecting member 20 with the distal end 40 is in the range of approximately 2½ inches to approximately five inches, and most preferably is approximately 2½ inches. These dimensions provide the appliance 10 with enough length to displace the water-tight cap 50 far enough away from the proximal body 60 of the endoscope to prevent unnecessary interference with use of the endoscope during its operation, while having a length short enough to accomplish the same purpose by avoiding unnecessary and excessive movement of the water-tight cap 50. In addition, in this embodiment and version of the invention, the width of the connecting member 20 measured perpendicular to the longitudinal axis is preferably in the range of approximately 5/16 inches to approximately 7/16 inches, and most preferably is approximately 6/16 inches. This width provides adequate structural strength for the appliance 10 to accomplish its purpose, while allowing the connecting member 20 to have sufficient flexibility. Further, in this embodiment and version of the invention, the connecting member 20 preferably has the same thickness as the distal end 40 and proximal end 30 (a thickness in the range of approximately 0.05 inches to approximately 0.15 inches), to simplify manufacturing of the appliance 10. This thickness provides sufficient structural strength for the appliance 10 to accomplish its purpose.

In the embodiments of the version of the invention illustrated in FIG. 1A, FIG. 2, and FIG. 3, the appliance 10 is constructed of a flexible polymer material, which may be of any color. Preferably, the appliance 10 is comprised of latex-free, neoprene rubber having a minimum tensile strength of 1,000 pounds per square inch, 400% ultimate elongation, 40-A shore +/−5 standard, and an operational temperature range of 0° to 250° Fahrenheit. In addition, the neoprene rubber preferably has excellent rebound and abrasion resistance, good compression set, tear resistance, and sunlight tolerance, and fair oil and solvent tolerance. In other embodiments of the version of the invention illustrated in FIG. 1A, FIG. 2, and FIG. 3, the appliance 10 further comprises an antibacterial coating on all of the surfaces thereof.

Figure 1B:
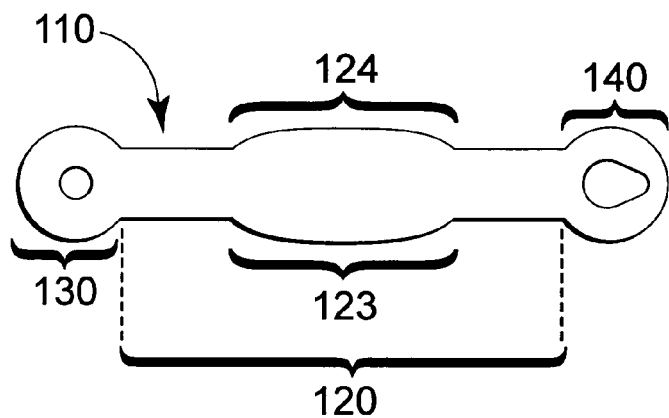
FIG. 1B is a plan view of another embodiment of the version of the invention illustrated in FIG. 1A.

Another embodiment of this version of the invention is the appliance 110 illustrated in FIG. 1B. In this embodiment, the connecting member 120 further comprises portions 123, 124 that protrude outwardly from each of the two longest sides of the rectangle comprising the connecting member 120. The purpose of the protruding portions 123, 124 is to provide additional space for specifying use, source or other information on the appliance 110 in written form. Although the protruding portions 123, 124 illustrated in FIG. 1B are generally elliptical in shape and are centered about the midpoint of the sides of the rectangle comprising the connecting member 120, which is the preferred shape, almost any other shape may be used. It is preferred, however, that the protruding portions do not cause the connecting member 120 to be less than the minimum preferred width (approximately 5/16 inches) or wider than the diameter of either the proximal end 130 or the distal end 140. In this embodiment of the invention, the characteristics of the proximal end 130 and the distal end 140 and all other aspects of the connecting member 120 are substantially the same as those of the proximal end 30, distal end 40, and connecting member 20, respectively, as described and illustrated in connection with FIG. 1A, FIG. 2, and FIG. 3, above. Further, the protruding portions 123, 124 preferably have the same thickness as and are constructed of the same material as the connecting member 120.

Figure 5:
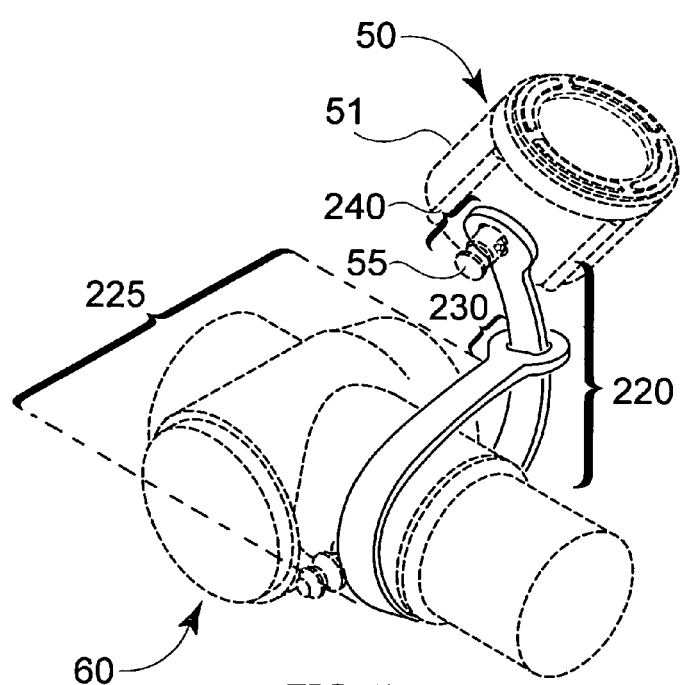
FIG. 5 is a perspective view of the version of the invention illustrated in FIG. 4, with the appliance removably connected to the water-tight cap and removably connected to the proximal body of an endoscope using a "wrap-around" connection, the water-tight cap and the proximal body being illustrated for reference only.
Figure 4:
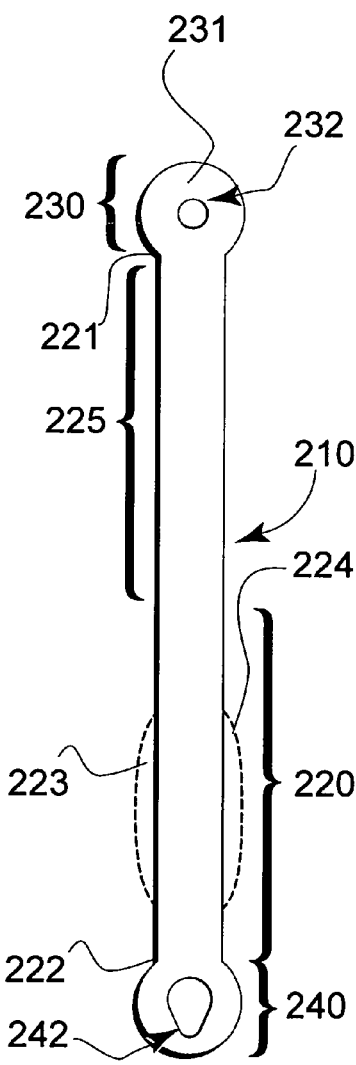
FIG. 4 is a plan view of a second version of the invention.

In another version of the invention, as illustrated in FIG. 4, the proximal end 230 is comprised of a disc 231 that is approximately circular in shape and an elongated portion 225 of the connecting member 220. The elongated member 225 is an extension of the connecting member 220, being located between the connecting member 220 and the disc 231 comprising the proximal end 230. In this version of the invention, as illustrated in FIG. 5, the elongated portion 225 and the disc 231 comprising the proximal end 230 are wrapped around the proximal body 60 of the endoscope and the distal end 240 is pulled through the aperture 232 in the proximal end 230 until the proximal end 230 is held tightly against the surface of the proximal body 60 of the endoscope. The periphery of the disc 231 preferably has a diameter of approximately 10/16 inches. The disc 231 also has an aperture 232 therein that is approximately circular in shape, preferably having a diameter in the range of approximately 3/16 inches to 5/16 inches, and most preferably is approximately 4/16 inches. This dimension allows for the distal end 240 to be passed through the aperture 232 in the proximal end 230, while still providing for adequate structural strength for the proximal end 230 to hold the proximal body 60 of the endoscope. In all other respects, the proximal end 230 and the distal end 240 in this version of the invention are substantially the same as the proximal end 30 and distal end 40, respectively, as described and illustrated in connection with FIG. 1A, FIG. 2, and FIG. 3, above.

In the version of the invention illustrated in FIG. 4 and FIG. 5, the connecting member 220 and the elongated portion 225 are generally in the shape of a rectangle. As a practical matter, there is continuity between the connecting member 220 and the elongated portion 225. The sum of the lengths of the connecting member 220 and the elongated portion 225 between the point of connection 222 of the connecting member 225 with the distal end 240 and the point of connection 221 of the elongated portion 225 with the proximal end 230 is preferably in the range of approximately seven inches to approximately nine inches, and most preferably is approximately seven inches. These dimensions provide the appliance 210 with enough length to displace the water-tight cap 50 far enough away from the proximal body 60 of the endoscope to prevent unnecessary interference with use of the endoscope during its operation, while having a length short enough to accomplish the same purpose by avoiding unnecessary and excessive movement of the water-tight cap 50. In addition, the width of the connecting member 220 and the elongated portion 225 measured perpendicular to their longitudinal axes is the same and is preferably in the range of approximately 5/16 inches to approximately 7/16 inches, and most preferably is approximately 6/16 inches. This width provides adequate structural strength for the appliance 10 to accomplish its purpose, while allowing the connecting member 220 and the elongated portion 225 to have sufficient flexibility. In all other respects, the elongated portion 225 has substantially the same characteristics as the connecting member 220 in this version of the invention, which has substantially the same characteristics as the connecting member 20 described and illustrated in connection with FIG. 1A, FIG. 2, and FIG. 3, above. In another embodiment of the version of the invention illustrated in FIG. 4 and FIG. 5, the connecting member 220 further comprises portions 223, 224 that protrude outwardly from each of the two longest sides of the rectangle comprising the connecting member 220, wherein such protruding portions 223, 224 are preferably generally elliptical in shape and are centered about the midpoint of such sides. These protruding portions 223, 224 may be of different shapes, and generally have substantially the same characteristics as the protruding portions 123, 123, as described and illustrated above in connection with FIG. 1B.

The present invention also includes a method of using the version of the invention described and illustrated above in connection with FIG. 1A, FIG. 2, and FIG. 3. This method for connecting the appliance 10 to an endoscope is comprised of the following steps: (1) removing the leak testing cap 55 from the venting connector 52 on the water-tight cap 50; (2) placing the aperture 42 of the distal end 40 over the venting connector 52, stretching the aperture 42 of the distal end 40 of the appliance 10 over the venting connector 52, sliding the distal end 40 along the sides of the venting connector 52 until the distal end 40 is adjacent to the surface of the body 51 of the water-tight cap 50, and removably attaching the leak testing cap 55 to the venting connector 52; and (3) stretching the proximal end 30 of the appliance 10 over the "S" connector 61 on the proximal body 60 of the endoscope, and sliding the proximal end 30 along the "S" connector 61 until the proximal end 30 is adjacent to the surface of the proximal body 60 of the endoscope. Steps (1) through (3), above, can be performed in any order. The appliance 10 can be removed by reversing the above steps (1) through (3) in any order.

A method for connecting the appliance 210, as described and illustrated above in connection with FIG. 4 and FIG. 5, to an endoscope is comprised of the following steps: (1) wrapping the proximal end 230 around the proximal body 60 of the endoscope, placing the distal end 240 through the aperture 232 in the proximal end 230, and pulling the distal end 240 through the aperture 232 in the proximal end 230 until the proximal end 230 is held tightly against the surface of the proximal body 60 of the endoscope; and (2) removing the leak testing cap 55 from the venting connector 52 on the water-tight cap 50, placing the aperture 242 of the distal end 240 over the venting connector 52, stretching the distal end 240 of the appliance 210 over the venting connector 52, sliding the distal end 240 along the venting connector 52 until the distal end 240 is adjacent to the surface of the body 51 of the water-tight cap 50, and removably attaching the leak testing cap 55 to the venting connector 52. Steps (1) and (2) in this method are to be performed in the order presented. The appliance 210 may be removed by reversing steps (1) and (2) of this method in the order presented.

What is claimed is:

1. An appliance for removably connecting a water-tight cap of an endoscope to a proximal body of such endoscope, such appliance being comprised of:
   (a) a connecting member portion;
   (b) a proximal end portion located at one end of the connecting member portion, wherein the proximal end portion is adapted to be removably connected to the proximal body of the endoscope; and
   (c) a distal end portion located at an end of the connecting member portion opposite from the proximal end portion, wherein the distal end portion is adapted to be removably connected to the water-tight cap of the endoscope; wherein the water-tight cap of the endoscope also has a venting connector comprised of a generally cylindrical or conical metal connector and a pin, such venting connector being attached to a body of the water-tight cap and receiving a leak testing cap that is adapted to fit over and be removably attached to the venting connector, and wherein the distal end portion is comprised of a disc with a perimeter that is approximately circular in shape, such disc having an aperture therein of a shape and size adapted to fit over the metal connector and pin of the venting connector so that the distal end portion is held adjacent to the surface of the water-tight cap when the leak testing cap is removably attached to the venting connector.

2. The appliance of claim 1, wherein the aperture is approximately "tear drop" in shape, so that an elongated portion of the aperture is adapted to fit over the pin of the venting connector.

3. The appliance of claim 2, wherein the distal end portion has a thickness in the range of approximately 0.05 inches to approximately 0.15 inches.

4. The appliance of claim 3, wherein the diameter of the outer periphery of the disc comprising the distal end portion is approximately 10/16 of an inch.

5. The appliance of claim 4, wherein the length of the aperture in the distal end portion longitudinally along the longest axis of the aperture is approximately 6/16 of an inch, and the length of such aperture axially along the shortest axis of the aperture is approximately 4/16 of an inch.

6. The appliance of claim 3, wherein the proximal body of the endoscope also has an "S" connector as a part thereof that is generally cylindrical or conical in shape and has a diameter greater at the distal end of the "S" connector than the diameter of the "S" connector adjacent to the surface of the proximal body of the endoscope, and wherein the proximal end portion of the connecting member portion is comprised of a disc with a perimeter that is approximately circular in shape, such disc having an aperture therein having a shape and size adapted to fit over and slide along the "S" connector until such disc is adjacent to the surface of the proximal body of the endoscope, so that the proximal end of the connecting member portion is held adjacent to the surface of the "S" connector while the proximal end portion of the connecting member portion is adjacent to the surface of the proximal body of the endoscope.

7. The appliance of claim 6, wherein the proximal end of the connecting member portion has a thickness in the range of approximately 0.05 inches to approximately 0.15 inches.

8. The appliance of claim 7, wherein the diameter of the outer periphery of the disc comprising the proximal end portion is approximately 10/16 of an inch.

9. The appliance of claim 8, wherein the aperture within the proximal end portion is approximately circular and has a diameter in the range of approximately 3/16 of an inch to approximately 4/16 of an inch.

10. The appliance of claim 6, wherein the connecting member portion is generally shaped as a rectangle.

11. The appliance of claim 10, wherein the length of the connecting member portion between the points of connection of the connecting member portion with the proximal end portion and the distal end portion is in the range of approximately 2½ inches to approximately 5 inches when measured along the longitudinal axis of the connecting member portion and the width of the connecting member portion is in the range of approximately 5/16 of an inch to approximately 7/16 of an inch when measured perpendicular to the longitudinal axis.

12. The appliance of claim 11, wherein the connecting member portion further comprises portions that protrude outwardly from each of the two longest sides of the rectangle comprising the connecting member portion.

13. The appliance of claim 12, wherein the protruding portions are generally elliptical in shape and are centered about the midpoint of such longest sides.

14. The appliance of claim 6, wherein the appliance is comprised of a flexible polymer material.

15. The appliance of claim 14, wherein the appliance is comprised of latex-free, neoprene rubber.

16. The appliance of claim 15, further comprising an antibacterial coating on all of the surfaces of the appliance.

17. The appliance of claim 3, wherein the proximal end portion is further comprised of:
   (a) a disc portion that is approximately circular in shape, having an aperture therein that is approximately circular in shape with a diameter in the range of approximately 3/16 of an inch to approximately 4/16 of an inch, and wherein the diameter of the periphery of the disc is approximately 10/16 of an inch; and (b) an elongated portion of the connecting member portion, which is an extension of the connecting member portion, such elongated portion being located between the connecting member portion and the disc comprising the proximal end portion;

(c) wherein the elongated portion and the disc comprising the proximal end portion are wrapped around the proximal body of the endoscope and the distal end portion is pulled through the aperture in the proximal end portion until the proximal end portion is held tightly against the surface of the proximal body of the endoscope.

18. The appliance of claim 17, wherein the connecting member portion and the elongated portion are generally shaped as a rectangle.

19. The appliance of claim 18, wherein the sum of the length of the connecting member portion and the elongated portion between the point of connection of the connecting member portion with the distal end portion and the point of connection of the elongated portion with the proximal end portion is in the range of approximately 7 inches to 9 inches when measured along the longitudinal axis of the connecting member portion and the elongated portion and the widths of the connecting member portion and the elongated portion are the same and in the range of approximately 5/16 of an inch to 7/16 of an inch when measured perpendicular to the longitudinal axis.

20. The appliance of claim 19, wherein the connecting member portion further comprises portions that protrude outwardly from each of the two longest sides of the rectangle comprising the connecting member portion.

21. The appliance of claim 20, wherein the protruding portions are generally elliptical in shape and are centered about the midpoint of such longest sides.

22. The appliance of claim 18, wherein the appliance is comprised of a flexible polymer material.

23. The appliance of claim 22, wherein the appliance is comprised of latex-free, neoprene rubber.

24. The appliance of claim 23, further comprising an antibacterial coating on all of the surfaces of the appliance.

25. A method of connecting the appliance of claim 6 to the water-tight cap and the proximal body of the endoscope, such method comprising the steps of:

(a) removing the leak testing cap from the venting connector on the water-tight cap;

(b) placing the aperture of the distal end portion over the venting connector, stretching the aperture of the distal end portion of the appliance over the venting connector, sliding the distal end portion along the venting connector until the distal end portion is adjacent to the surface of the body of the water-tight cap, and removably attaching the leak testing cap to the venting connector; and (c) stretching the aperture of the proximal end portion of the appliance over the "S" connector on the proximal body of the endoscope, and sliding the proximal end portion along the "S" connector until the proximal end portion is adjacent to the surface of the proximal body of the endoscope.

26. A method of connecting the appliance of claim 17 to the water-tight cap and the proximal body of the endoscope, such method comprising the steps of:

(a) wrapping the proximal end portion around the proximal body of the endoscope, placing the distal end portion through the aperture in the proximal end portion, and pulling the distal end portion through the aperture in the proximal end portion until the proximal end portion is held tightly against the surface of the proximal body of the endoscope; and (b) removing the leak testing cap from the venting connector on the water-tight cap, placing the aperture of the distal end portion over the venting connector, stretching the aperture of the distal end portion of the appliance over the venting connector, sliding the distal end portion along the venting connector until the distal end portion is adjacent to the surface of the body of the water-tight cap, and removably attaching the leak testing cap to the venting connector.

* * * * *